United States Patent [19]

Leibinsohn

[11] Patent Number: 5,232,435
[45] Date of Patent: Aug. 3, 1993

[54] SPLINT

[76] Inventor: Saul Leibinsohn, 24 Lipski Street, 62 195 Tel Aviv, Israel

[21] Appl. No.: 831,012

[22] Filed: Feb. 4, 1992

[51] Int. Cl.$^5$ .............................................. A61F 5/04
[52] U.S. Cl. ......................................... 602/16; 602/20
[58] Field of Search .................... 602/5, 4, 12, 16, 21, 602/26, 27, 20, 878

[56] References Cited

U.S. PATENT DOCUMENTS

| Re. 30,501 | 2/1981 | Almeida | 662/26 X |
|---|---|---|---|
| 4,340,641 | 6/1982 | Frank | 602/26 X |
| 4,485,808 | 12/1984 | Hepburn | 602/5 |
| 4,807,609 | 2/1987 | Meals | 602/20 |
| 4,941,465 | 7/1990 | Borschneck | 602/16 X |

Primary Examiner—Robert A. Hafer
Assistant Examiner—Brian E. Hanlon
Attorney, Agent, or Firm—Benjamin J. Barish

[57] ABSTRACT

A splint includes a pair of hingedly-mounted frame sections for receiving the two limbs of the patient. Each frame section includes two frame members secured together to occupy a common plane, and an intermediate member pivotally mounted to the first frame member from an inoperative position in the common plane between the frame members, either to a first operative position on one side of the common plane or to a second operative position on the other side of the common plane. A flexible strip is joined between the second frame member and the intermediate member, and is of a width larger than the spacing between the frame members so as to form a curved bed for supporting the right limb of the patient when the intermediate member is in its first operative position, or the left limb of the patient when the intermediate member is in its second operative position.

16 Claims, 3 Drawing Sheets

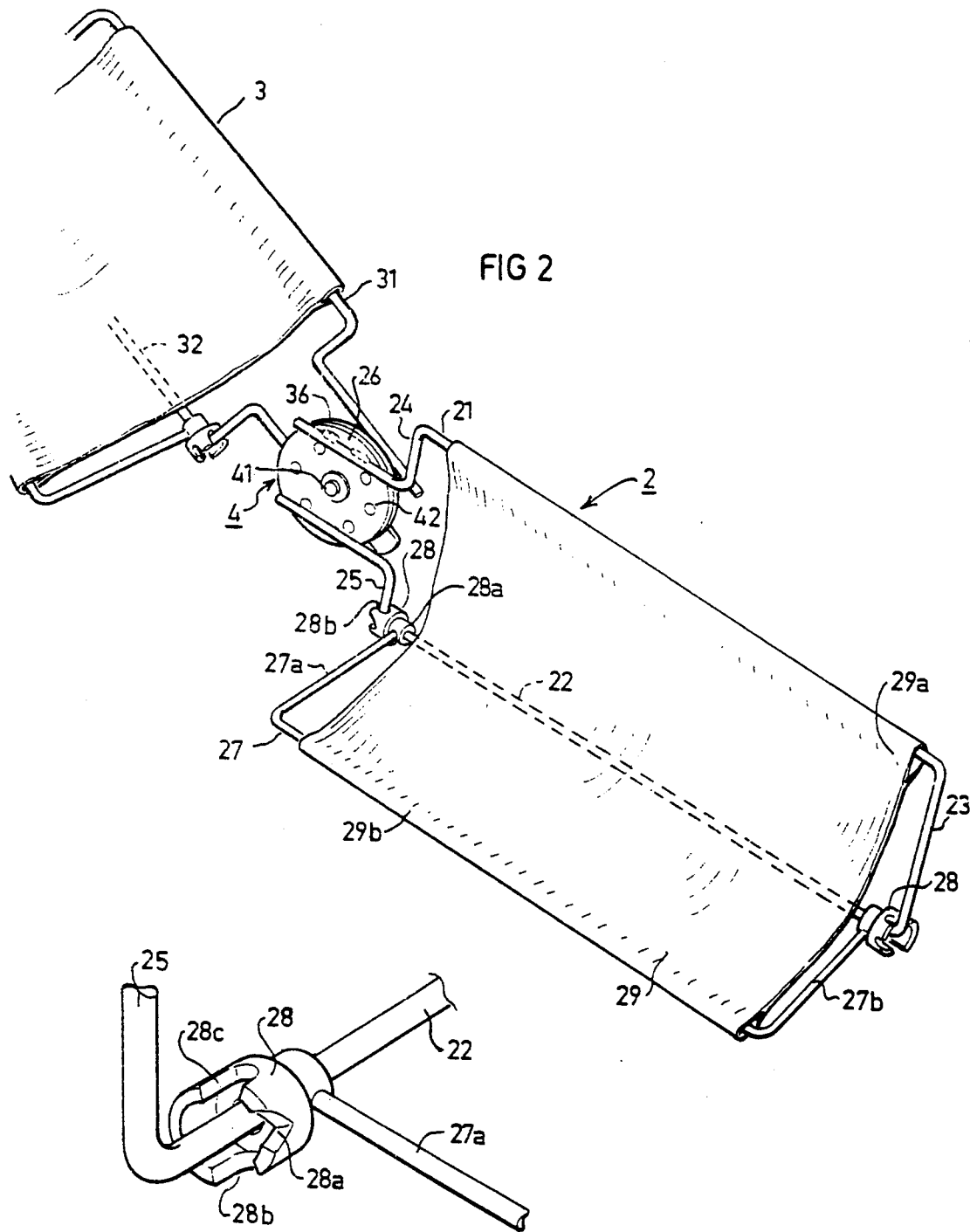

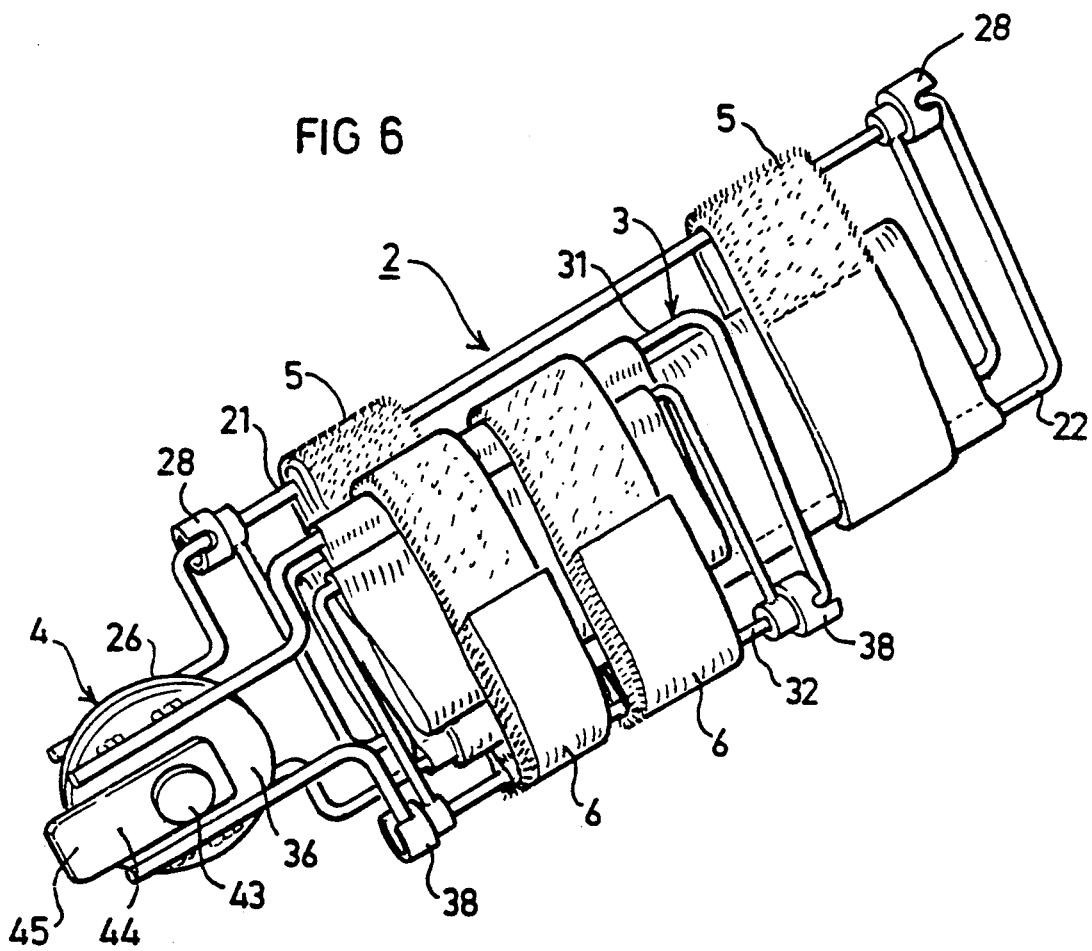

SPLINT

FIELD AND BACKGROUND OF THE INVENTION

The invention relates to splints for immobilizing limbs of a patient, e.g., when a limb has been fractured. The invention is particularly useful for immobilizing fractured arms, and is therefore described below with respect to this application, but it will be appreciated that the invention could also be used with respect to fractured legs.

Many types of splints are available. In some constructions, one splint is provided for a left limb (e.g., arm) and another for a right limb. Other known constructions are relatively complicated or bulky, or are made of deformable materials and therefore not sufficiently rigid, or do not permit convenient adjustment of the angle at which the two limbs (e.g., upper/lower arms) are to be immobilized.

OBJECTS AND BRIEF SUMMARY OF THE INVENTION

An object of the present invention is to provide a splint having advantages in one or more of the above respects.

More particularly, an object of the present invention is to provide a splint which may be used for immobilizing either a right limb (e.g., arm) or a left limb, which enables convenient adjustment of the angle at which the two limbs are to be immobilized, and which is of a simple and compact construction so as to take up a small volume when the splint is in its inoperative condition.

According to one aspect of the present invention, there is provided a splint for immobilizing either a right limb or a left limb of a patient, comprising: a rigid frame including first and second spaced, longitudinally-extending, frame members secured together to occupy a common plane; and a rigid, longitudinally-extending intermediate member pivotally mounted to the first frame member from an inoperative position in the common plane between the frame members, either to a first operative position on one side of the common plane or to a second operative position on the other side of the common plane. The splint further includes a flexible strip joined at one edge to the second frame member and at its opposite edge to the intermediate member. The flexible strip is of a width larger than the spacing between the frame members so as to form a curved bed for supporting the right limb of the patient when the intermediate member is in its first operative position, or the left limb of the patient when the intermediate member is in its second operative position.

According to another aspect of the present invention, there is provided a splint for immobilizing two limbs of a patient on opposite sides of a hinged joint, comprising: a pair of rigid frame sections hingedly mounted at one of their ends for receiving the two limbs of the patient, and straps carried by the frame sections for securing each limb to its respective frame section, wherein each of the frame sections includes the features set forth above.

According to a still further aspect of the present invention, there is provided a splint comprising a pair of rigid frame sections hingedly mounted at one of their ends by a pair of discs each secured to one of the rigid frame sections and rotatably mounted to each other about a common axis. One of the discs is formed with a plurality of detents cooperable with a locking element carried by the other disc for locking the two discs, and thereby their respective frame sections, in any one of a plurality of angular positions with respect to each other.

As will be described more particularly below, a splint constructed in accordance with the foregoing features may be conveniently used for both right limbs or left limbs, and conveniently enables adjustment of the angle at which the two limbs are to be immobilized. The foregoing features also enable a simple and sturdy construction, and particularly one which is compact when in its inoperative position, thereby facilitating the storing, transporting, and/or handling of such splints. A further advantage is that the splint may be applied not only in the conventional manner to engage the under surface of the limb (e.g., arm), but may also be applied to engage the upper surface of the limb, for example, where the under surface is badly injured or has to be exposed for treatment or the like.

Further features and advantages of the invention will be apparent from the description below.

BRIEF DESCRIPTION OF THE DRAWINGS

The invention is herein described, by way of example only, with reference to the accompanying drawings, wherein:

FIG. 2 illustrates the splint of FIG. 1 alone, as viewed from the top;

FIG. 5 is an enlarged fragmentary view illustrating one of the rod clamps included in the splint of FIGS. 1 and 2 to permit the use of the splint for right limbs as well as left limbs; and FIG. 6 illustrates the splint of FIGS. 1 and 2 in its inoperative, collapsed condition, for storage or handling.

DESCRIPTION OF A PREFERRED EMBODIMENT

Figure 1:
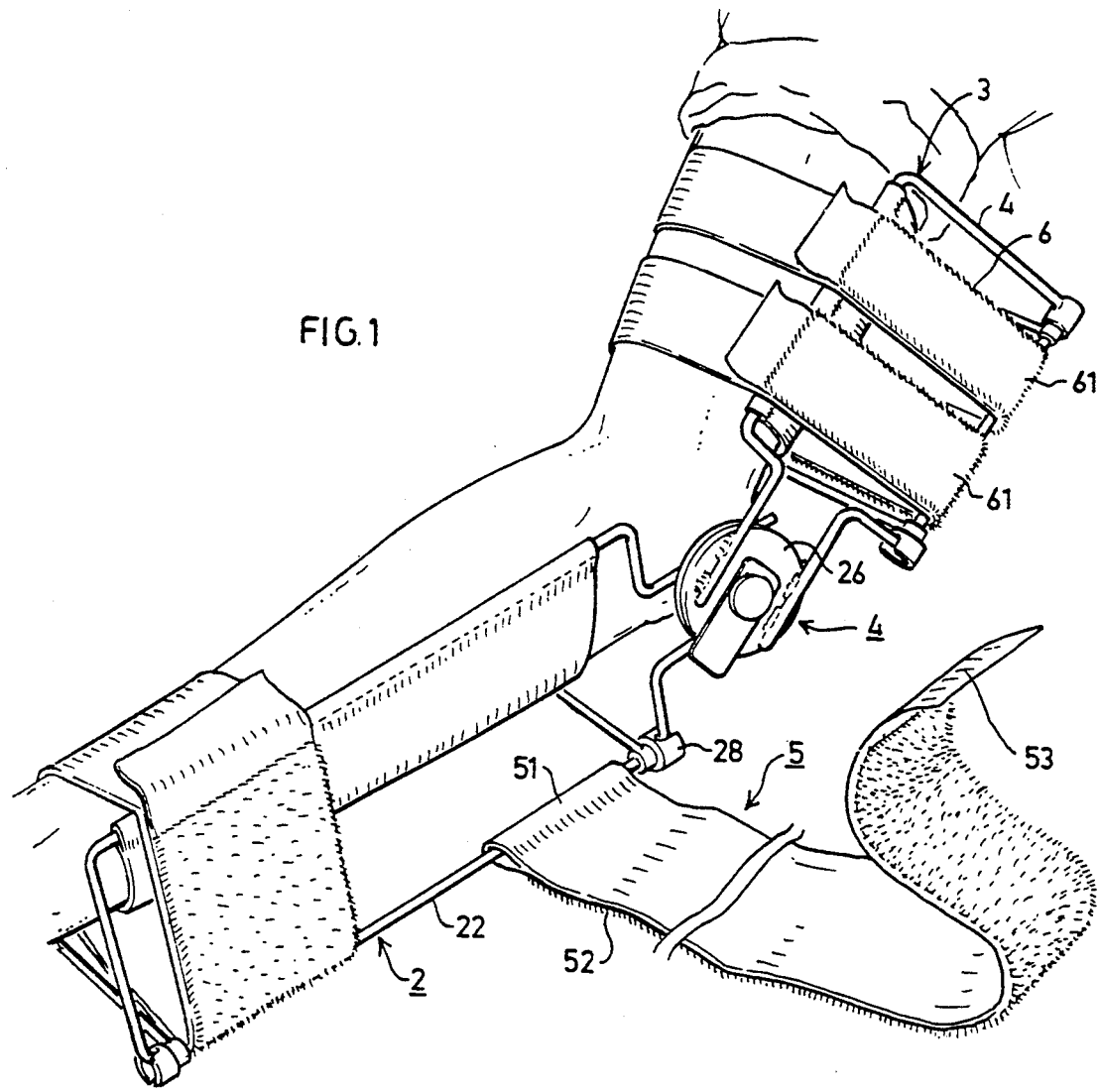
FIG. 1 illustrates one form of splint constructed in accordance with the present invention as applied to the right arm of a patient as viewed from the bottom.

The splint illustrated in the drawings is intended particularly for use with a fractured arm, either the left arm or the right arm. FIG. 1 illustrates its condition when applied to the right arm, and as viewed from the bottom to better show its structure.

The illustrated splint includes two rigid frame sections 2, 3, hingedly mounted at one of their ends by a hinge 4. Frame section 2 is adapted to receive the lower arm of the patient, and is therefore longer in length than frame section 3 adapted to receive the upper arm. Otherwise, the two frame sections 2, 3 are of substantially the same construction. The lower frame section 2 includes a pair of straps, generally designated 5, for securing the lower arm to the lower frame section 2; and similarly the upper frame section 3 includes a pair of straps, generally designated 6, for securing the upper arm to the upper frame section 3.

When the splint is applied to a patient, hinge 4 occupies the patient's elbow. The hinge is of a construction which permits the two frame sections 2, 3 to be fixed at any angular position with respect to each other.

Frame section 2 includes a rigid frame constituted of a rod which is bent to form a pair of longitudinally-extending frame members 21, 22 joined to each other at their outer end by a right-angle leg 23, and joined at their inner ends (occupied by the hinge 4), by two right-angle legs 24, 25. Thus, the two right-angle legs 24, 25 are fixed to a disc 26, as by welding.

Frame section 2 further includes a longitudinally-extending intermediate member 27, also in the form of a rod, which is pivotally mounted to frame member 22. For this purpose, the opposite ends of the intermediate member 27 are turned inwardly at a right-angle, and carry rod clamps 28 formed with openings receiving frame member 22, so that, when the outer ends of the legs 27a, 27b are squeezed towards each other, the rod clamps 28 also move towards each other. The outer faces of the rod clamps 28 are formed with three notches, as shown at 28a, 28b, 28c, adapted to selectively receive the respective right-angle legs 25 of leg 23 of frame member 22 (or frame member 21 at the opposite end), when the two legs 27a, 27b of the intermediate frame member 27 are squeezed towards each other and then released. As will be described below, the three notches 28a-28c of the rod clamps 28 determine three positions of the intermediate frame member 27.

Frame section 2 further includes a flexible strip 29 joined at one edge 29a to frame member 21, and at the opposite edge 29b to the intermediate member 27. Flexible strip 29, e.g., of suitable fabric or plastic, is of a width greater than the space between the two frame members 21, 22.

In frame section 3, which is of the same construction as frame section 2 except of shorter length, the elements corresponding to elements 20-29 in frame section 2 are correspondingly numbered 30-39.

Figure 3:
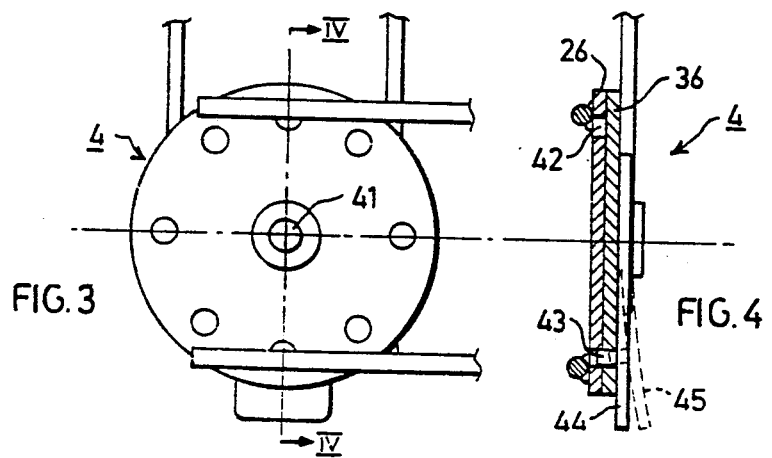
FIG. 3 is an enlarged view illustrating the hinge between the two frame sections in the splint of FIGS. 1 and 2.
Figure 4:
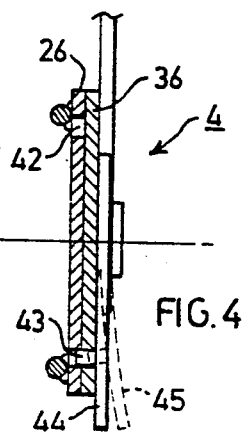
FIG. 4 is a sectional view along line IV—IV of FIG. 3.

Disc 26 of frame section 2 is rotatably mounted with respect to disc 36 of frame section 3 about a central axis, shown at 41 in FIGS. 2 and 3. Disc 26 is formed with a circular array of holes 42, which serve as detents in cooperation with locking element 43 (FIG. 4) carried by disc 36 for locking the two discs in any desired angular position with respect to each other. Locking element 43 is in the form of a pin at the end of a flexible arm 44 secured to disc 36. Arm 44 also includes a fingerpiece 45 projecting outwardly of the two discs 26, 36, to facilitate moving locking pin 43 into or out of one of the selected holes 42 in disc 26. Disc 36 is formed with a single hole, as shown at 46 in FIG. 4, through which the locking pin 43 passes when received in a selected one of the locking holes 42 in disc 26.

The two straps 5 carried by the lower frame section 2 are formed at one of their ends with loops 51 which freely receive frame member 22. The inner faces of these loops are preferably treated or covered to form a non-slip surface to inhibit sliding of the straps. These straps include Velcro (Reg. T.M.) type fasters to permit the strap to be wrapped around the lower arm when applied to frame section 2. Thus, the inner part of each strap is formed with hooks, as shown at 52, on one surface of the strap, and the outer end of the opposite surface of the strap is formed with loops 53, permitting the strap to be wound around the limb in the frame section and then secured by pressing the hooks 53 into engagement with the loops 52.

The straps 6 carried by the upper frame section 3 are similarly constructed, and are correspondingly numbered 61-63 to facilitate understanding.

The splint illustrated in the drawings may be used in the following manner:

When the splint is in its inoperative condition, as illustrated in FIG. 6, the two intermediate members 27 and 37 are pivoted so that each occupies the same plane as the frame members 21, 22 in the respective frame section. In this position, the rod clamps 28, 38 carried at the ends of the arms of the intermediate members 27, 37, receive the legs 23, 25 and 33, 35, respectively, in the middle notch (e.g., 28a, FIG. 5) of the rod clamp. In addition, the two frame sections 2, 3 are pivoted about hinge 4 to overlie each other, as shown in FIG. 6. A very compact arrangement is thus provided by this folded condition of the splint, facilitating its storge and handling.

When the splint is to be used for immobilizing a right arm, the two frame sections 2, 3 are pivoted to an open condition. This is done by pressing fingerpiece 45 (FIG. 4) to move locking pin 43 out of the hole disc 26 42 in which it had been previously received. This permits the two frame sections 2, 3 to be rotated with respect to each other, and as soon as the desired angular position is reached, fingerpiece 45 is released, whereupon locking pin 43 moves into the hole 42 of disc 26 corresponding to the selected angular position of the two frame sections.

The lower arm is then applied to the lower frame section 2 as follows: First, the intermediate member 27 is pivoted out of the plane of the frame members 21 22, by gently squeezing the outer ends of the two legs 27a, 27b of the intermediate member 27 towards each other to cause its rod clamps 28 to release from the legs 23 and 25 at the opposite ends of frame section 2. The intermediate member 27 may thus be pivoted 90° from its normal position coplanar with the frame members 21, 22, and may be locked in this position by releasing the ends of legs 27a, 27b, whereupon the rod clamps 28 return to their normal positions and engage the outer legs 23, 25 of the frame section 2.

When the splint is to be used for a right arm fracture, as shown in FIG. 1, intermediate member 27 is pivoted to the position illustrated in FIG. 1 wherein the end legs 23, 25 seat within notches 28b of the rod clamps 28. On the other hand, if the splint is to be used for a left arm fracture, intermediate member 27 is pivoted in the opposite direction, as shown in FIG. 2, to cause the end legs 23, 25 to seat within notches 28c of the rod clamps 28.

In either of the latter two operative positions of the intermediate member 27, the flexible strip 29 forms a curved bed for providing a good anatomical and axial support for the limb of the patient. The two Velcro straps 5 are then applied to fix the lower arm to the frame section 2.

The upper arm is then applied in the same manner to the upper frame section 3.

If, in applying the splint to the patient, it is desirable to readjust the angle between the two frame sections, this may easily be done by pressing fingerpiece 45 (FIG. 4) outwardly to unseat locking pin 43 from the locking hole 42 in which it had been previously seated, pivoting the two frame sections, and then releasing fingerpiece 45 to securely lock the two frame sections in the new angular position.

While the invention has been described with respect to the use of the splint for fractured arms, it wil be appreciated that the same basic construction can also be used for fractured legs. Many other variations, modifications and applications of the invention will be apparent.

What is claimed is:

1. A splint for immobilizing either a right limb or a left limb of a patient, comprising:
   a rigid frame including first and second spaced, longitudinally-extending, frame members secured together to occupy a common plane;
   a rigid longitudinally-extending intermediate member pivotally mounted to said first frame member from an inoperative position in said common plane between said frame members, either to a first operative position on one side of said common plane or to a second operative position on the other side of said common plane;
   and a flexible strip joined at one edge to said second frame member and at its opposite edge to said intermediate member;
   said flexible strip being of a width larger than the spacing between said frame members so as to form a curved bed for supporting the right limb of the patient when the intermediate member is in its first operative position, or the left limb of the patient when the intermediate member is in its second operative position.

2. The splint according to claim 1, wherein said intermediate member is pivotal 90° with respect to said first frame member to either said first or second operative positions.

3. The splint according to claim 1, wherein said first and second frame members are rods, and said intermediate member is also a rod having a pair of right-angle legs at its opposite ends pivotal to said first frame member rod.

4. The splint according to claim 3, wherein said first and second frame members are joined at their opposite ends by right-angle legs, said intermediate member carrying a rod clamp at the end of each of its right-angle legs engageable with the right-angle legs of the first and second frame members to clamp the intermediate member to its inoperative position or to either of its operative positions.

5. The splint according to claim 4, wherein said right-angle legs of the intermediate member are flexible to permit movement of their rod clamps towards each other, each of said rod clamps being formed with a notch for said inoperative position and for each of said operative positions, for receiving the respective right-angle leg of the frame members to thereby clamp the intermediate member in a selected one of said positions.

6. The splint according to claim 1, further including a pair of straps secured at one of their ends to said first frame member and windable over the limb received on said flexible strip for securing the limb to the splint.

7. A splint for immobilizing two limbs on a patient on opposite sides of a hinged joint, comprising:
   a pair of rigid frame sections hingedly mounted at one of their ends for receiving the two limbs of the patient;
   and straps carried by said frame sections for securing each limb to its respective frame section;
   each of said frame sections comprising:
   a rigid frame including first and second spaced, longitudinally-extending, frame members secured together to occupy a common plane;
   a longitudinally-extending intermediate member having a pair of legs at its opposite ends pivotally mounted to said first frame member from an inoperative position in said common plane between said frame members, either to a first operative position on one side of said common plane or to a second operative position on the other side of said common plane;
   and a flexible strip joined at one edge to said second frame member and at its opposite edge to said intermediate member;
   said flexible strip being of a width larger than the spacing between said frame members so as to form a curved bed for supporting the right limb of the patient when the intermediate member is in its first operative position, or the left limb of the patient when the intermediate member is in its second operative position.

8. The splint according to claim 7, wherein said intermediate member is pivotal 90° and with respect to said first frame member to either said first or second operative positions.

9. The splint according to claim 7, wherein said first and second frame members are rods, and said intermediate member is also a rod having a pair of right-angle legs at its opposite ends pivotal to said first frame member rod.

10. The splint according to claim 9, wherein said first and second frame members are joined at their opposite ends by right-angle legs, said intermediate member carrying a rod clamp at the end of each of its right-angle legs engageable with the right-angle legs of the first and second frame members to clamp the intermediate member to its inoperative position or to either of its operative positions.

11. The splint according to claim 10, wherein said right-angle legs of the intermediate member are flexible to permit movement of their rod clamps towards each other under finger pressure, each of said rod clamps being formed with a notch for said inoperative position and for each of said operative positions, for receiving the respective right-angle leg of the frame members to thereby clamp the intermediate member in a selected one of said positions.

12. A splint for immobilizing two limbs of a patient on opposite sides of a hinged joint, comprising:
   a pair of rigid frame sections hingedly mounted at one of their ends for receiving the two limbs of the patient;
   and straps carried by said frame sections for securing each limb to its respective frame section;
   each of said pair of rigid frame sections being hingedly mounted at one of their ends by a pair of discs each secured to one of said rigid frame sections and rotatably mounted to each other about a common axis;
   one of said discs being formed with a plurality of detents cooperable with a locking element carried by the other of said discs for locking the two discs, and thereby their respective frame sections, in any one of a plurality of angular positions with respect to each other;
   said detents formed in said one disc being holes formed in a circular array in said one disc around said rotary axis;
   said locking element carried by said other disc being a pin fixed to the end of a displaceable arm carried by said other disc and receivable in a selected hole in said one disc;

said pin being movable through a hole formed in said other disc when moved into a selected hole in said one disc;

each of said frame sections comprising:

a rigid frame including first and second spaced, longitudinally-extending, frame members secured together to occupy a common plane;

a rigid longitudinally-extending intermediate member pivotally mounted to said first frame member from an inoperative position in said common plane between said frame members, either to a first operative position on one side of said common plane or to a second operative position on the other side of said common plane;

and a flexible strip joined at one edge to said second frame member and at its opposite edge to said intermediate member;

said flexible strip being of a width larger than the spacing between said frame members so as to form a curved bed for supporting the right limb of the patient when the intermediate member is in its first operative position, or the left limb of the patient when the intermediate member is i its second operative position.

13. The splint according to claim 12, wherein said displaceable arm includes a fingerpiece projecting outwardly of said discs to facilitate moving the arm.

14. The splint according to claim 12, wherein said intermediate member is pivotal 90° with respect to said first frame member to either said first or second operative positions.

15. The splint according to claim 12, wherein said first and second frame members are rods, and said intermediate member is also a rod having a pair of right-angle legs at its opposite ends pivotal to said first frame member rod.

16. The splint according to claim 15, wherein said first and second frame members are joined at their opposite ends by right-angle legs, said intermediate member carrying a rod clamp at the end of each of its right-angle legs engageable with the right-angle legs of the first and second frame members to clamp the intermediate member to its inoperative position or to either of its operative positions.

* * * * *